United States Patent [19]

Hüper et al.

[11] 4,113,941
[45] Sep. 12, 1978

[54] PROCESS FOR PURIFYING PRODUCTS OBTAINED FROM ENZYMATIC CLEAVAGE OF BETA-LACTAM ANTIBIOTICS

[75] Inventors: Fritz Hüper; Helmut Oberheiden, both of Wuppertal, Germany

[73] Assignee: Bayer Aktiengesellschaft, Leverkusen, Germany

[21] Appl. No.: 692,876

[22] Filed: Jun. 4, 1976

[30] Foreign Application Priority Data

Jun. 26, 1975 [DE] Fed. Rep. of Germany ........ 2528622

[51] Int. Cl.$^2$ .............................................. C07D 501/12
[52] U.S. Cl. ................... 544/20; 260/306.7 C
[58] Field of Search ................. 260/243 C, 306.7 C; 544/20

[56] References Cited

U.S. PATENT DOCUMENTS

| | | | |
|---|---|---|---|
| 3,049,541 | 8/1962 | Abraham et al. | 260/243 C |
| 3,184,454 | 5/1965 | Abraham et al. | 260/243 C |
| 3,207,755 | 9/1965 | Abraham et al. | 260/243 C |
| 3,733,320 | 5/1973 | Pines et al. | 260/243 C |

FOREIGN PATENT DOCUMENTS

| | | |
|---|---|---|
| 870,396 | 6/1961 | United Kingdom. |
| 891,173 | 3/1962 | United Kingdom. |
| 988,065 | 4/1965 | United Kingdom. |
| 1,212,551 | 11/1970 | United Kingdom. |

*Primary Examiner*—Nicholas S. Rizzo
*Attorney, Agent, or Firm*—Burgess, Dinklage & Sprung

[57] ABSTRACT

The reaction product from the enzymatic cleavage of amido side chains from $\beta$-lactam antibiotics is purified by contact with a polymeric adsorbent.

15 Claims, No Drawings

PROCESS FOR PURIFYING PRODUCTS OBTAINED FROM ENZYMATIC CLEAVAGE OF BETA-LACTAM ANTIBIOTICS

The present invention relates to a new process for purifying the end products obtained from the enzymatic cleavage of the amido side chains from β-lactam antibiotics, especially 6-aminopenicillanic acid (6-APA) and 7-amino-$\Delta^3$-cepham derivatives, which are valuable starting materials for the preparation of semi-synthetic β-lactam antibiotics.

It is generally customary to remove colored impurities with the aid of active charcoal. However, 6-APA and 7-amino-cepham derivatives are relatively strongly adsorbed by active charcoal and this naturally leads to considerable losses in yield, so that it is economically highly disadvantageous to purify 6-APA and 7-amino-cepham derivatives, or solutions containing these compounds, with active charcoal.

In accordance with the present invention it has been found that undesirable impurities contained in the reaction mixture after the enzymatic cleavage of β-lactam antibiotics can be removed by bringing the reaction solution into contact, optionally after removing the enzyme used, with polymeric adsorbents. The desired end products may subsequently be isolated according to generally customary methods, preferably to obtain the product in crystalline form. It is extremely surprising that it is possible, according to the process of the invention, in a simple manner to free the crude solutions obtained from the enzymatic cleavage of β-lactam antibiotics from impurities, particularly colored impurities, without a substantial amount of the desired end products being irreversibly adsorbed, such as is the case with an active charcoal adsorbent.

It is well known in the art that 6-APA or 7-aminodeacetoxy-cephalosporanic acid (7-ADCA) is adsorbed in a column filled with a strongly basic quarternary ammonium anion exchange resin in the form of the acetate and can be subsequently eluted with an aqueous solution of ammonium acetate (compare German Offenlegungsschrift No. 2,422,374 and British Patent Specification No. 892,144). However, these possible methods of adsorption can be employed only if the 6-APA or 7-ADCA solution contains no interfering constituents, but the crude solutions from enzymatic cleavage do, in fact, normally contain interfering anions. The methods of the state of the art therefore can not be employed in an economic manner for purifying the crude solutions obtained from enzymatic cleavage. It was therefore the more surprising, and not foreseeable, that the process according to the invention leads to very good results.

Compared with the known processes, the process according to the invention has the advantage that the desired end products are obtained without involved purification, for example by recrystallization, in high purity and, in particular, free from constituents which impart color, and in very good yield. In addition, the end products are obtained in crystalline form which is particularly favorable for industrial use. The process according to the invention thus represents a substantial enrichment of the art.

The starting material to be purified according to the present invention can be virtually any crude solution obtained according to the generally known enzymatic methods for cleavage of the side chain from β-lactam antibiotics, preferably the penicillins and cephalosporins (including derivatives). The nature and origin of the enzyme (for example microbial, such as bacterial, fungal or other animal or vegetable origin) is of no significance for carrying out the process according to the invention. The enzyme can have been either in the natural state or in a modified state. The enzymatic cleavage may have been carried out with the aid of intact or destroyed cells of microorganisms containing the enzyme or with the crude or purified enzyme and the enzyme can also be adsorbed on, covalently bonded to or, by means of bridging agents, crosslinked to polymeric carriers, for example water-insoluble or water-soluble polymeric carriers, or can be enclosed in any other desired form in polymeric carriers (for example encapsulated, spun in fibers, enclosed in the pores of polymers, and the like). Penicillinacylase is particularly preferred as the enzyme and the penicillinacylase from Escherichia coli bacteria may be mentioned in particular.

Both the antibiotics produced microbially in a natural manner, in a known way, and their derivatives can have been employed as the β-lactam antibiotics used for the enzymatic cleavage.

Penicillins and cephalosporins, as well as the derivatives of these compounds, are particularly suitable for the cleavage. Particularly preferred compounds which may be mentioned are: benzylpenicillin, phenoxymethylpenicillin, benzylcephalosporin, N-phenoxyacetyl-7-amino-cephalosporanic acid and 7-phenylacetamido-deacetoxycephalosporanic acid as well as such salts of these compounds with inorganic or organic bases as are suitable for enzymatic hydrolysis. Sodium, calcium and ammonium salts, or salts with aliphatic, araliphatic or aromatic primary, secondary and tertiary amines, such as, for example, ethylamine, triethylamine and hydroxyethylamine, and cyclic amines, such as, for example, pyridine, piperidine, morpholine, piperazine, N-methylpiperazine and N-ethylpiperidine are typical useful salts.

Benzylpenicillin, phenoxymethylpenicillin and 7-phenylacetamido-deacetoxycephalosporanic acid and the sodium and potassium salts of these compounds are very particularly preferred for use in the enzymatic splitting.

Crude solutions which are suitable to be purified by the process according to the invention can be obtained, for example, according to known procedures, such as described in the following publications: E. H. Flynn, Cephalosporins and Penicillins, Academic Press, New York 1972, especially pages 29 to 39; German Offenlegungschriften Nos. 2,157,970, 2,215,539, 2,215,687, 2,312,824, 2,212,276, 2,355,078, 2,409,569, 1,907,365 and 1,917,057; German Patent Specification No. 1,111,778 and U.S. Pat. No. 3,239,394. These publications also describe β-lactam antibiotics suitable for enzymatic cleavage.

Preferred end products of the purification process according to the invention are 6-APA, 7-ADCA and 7-aminocephalosporanic acid (7-ACA); 7-ADCA and 6-APA are particularly preferred.

Very diverse types of polymeric adsorbents can be employed for carrying out the purification process according to the invention. Preferred adsorbents are those which have a macroporous structure. Those polymeric adsorbents which have a macroporous structure and comprise a polystyrene skeleton crosslinked with divinylbenzene or which consist of such a skeleton are particularly preferred. Adsorbents which contain basic, preferably strongly basic, functional groups are particularly suitable. Among these adsorbents, macroporous anion exchangers with quaternary ammonium groups may be mentioned in particular. The quaternary ammonium groups can be bonded directly to nitrogen atoms of the carrier or indirectly via any desired divalent radical, for example alkylene with preferably 1 to 4 carbon atoms, such as methylene. The quaternary ammonium groups are suitably:

$$-\overset{R_1}{\underset{R_3}{\overset{|}{N}}}{}^{\oplus}-R_2$$

wherein $R_1$, $R_2$, $R_3$ are the same or different substituted or unsubstituted alkyl, e.g. alkyl of 1 to 4 carbon atoms. When $R_1$, $R_2$ or $R_3$ is substituted, the preferred substituent is hydroxy; the preferred alkyl is especially methyl or ethyl. In this context, $$-CH_2-\overset{\oplus}{N}(CH_3)_3 \quad \text{and} \quad -\overset{\oplus}{\underset{C_2H_4OH}{N}}(CH_3)_2$$

may be mentioned by way of example.

Possible ions of opposite charge include any anion usually present in such anion exchangers, especially strong anions, such as, for example, $Cl^-$, $NO_3^-$ and $SO_4^{2-}$. Hydroxyl ion is less suitable since, as the result of ion exchange, the solution to be treated becomes alkaline, in an undesirable manner.

The preferred adsorbents (based on polystyrene with a macroporous structure) are commercially available and obtainable, for example, under the following names:
Amberlite ® IRA 401 (Trademark of Rohm & Haas, USA)
Amberlite ® IRA 900 (Trademark of Rohm & Haas, USA)
Amberlite ® IRA 911 (Trademark of Rohm & Haas, USA)
Amberlite ® IRA 458 (Trademark of Rohm & Haas, USA)
Amberlyst ® A 29 (Trademark of Rohm & Haas, USA)
Dowex ® MSA 1 (Trademark of Dow Chemical Comp., USA)
Dowex ® 21 K (Trademark of Dow Chemical Comp., USA)
Lewatit ® MP 500 A (Trademark of Bayer AG, Leverkusen, Federal Republic of Germany).

In order to carry out the purification process according to the invention, the usually deeply brown colored crude solution, which is obtained direct from the enzymatic cleavage of β-lactam antibiotics, is brought into contact, preferably after removal of the enzyme and any undissolved constituents, in any desired manner with a suitable amount of the adsorbent. The crude solution can be poured through a column filled with the adsorbent. Alternatively, the crude solution can be mixed with the adsorbent in a stirred kettle, and when the purification is ended, the adsorbent is separated from the purified product by settling or by filtering off. Preferably, the reaction solution is filtered continuously through a column filled with the adsorbent. The capacity of the adsorbent can be utilized until the color content of the eluate exceeds a value which is set depending on the quality requirement and can be determined according to customary optical methods of measurement. The optimum feed rate for the crude solution to be decolorized and the geometry of the column to be used is empirically determined on the basis of the particular conditions of use, the apparatus available and the degree of purity of the starting material. Because of the simplicity of the process, it is easily possible for those skilled in the art to produce an optimum design of the purification unit without difficulty.

The following conditions, for example, have proved suitable in practice for the purification of 1 $m^3$ of reaction solution by column filtration:
feed rate: about 100 to 800 liters/hour, preferably 400 to 600 and especially 500 liters/hour
diameter of the column: about 5 to 20 cm, preferably 8 to 15 and especially 10 cm
height of the column packing: about 30 to 100 cm, preferably 40 to 80 and especially 60 cm.

Corresponding amounts of adsorbent have also been employed for other methods, for example in a stirred kettle.

The purification process according to the invention is carried out at temperatures at which the desired end products (preferably 6-APA, 7-ADCA and 7-ACA) are stable. Preferably, the process is carried out at temperatures of about +1° to about +50° C., especially at 10° to 40° C. Usually it will be particularly advantageous to carry out the process at room temperature (about 8° to 25° C.).

It is not necessary to maintain specific concentrations in order to carry out the process according to the invention. Concentrations which are optimum for carrying out the enzymatic cleavage that precedes the purification are preferred for use in the adsorption. Accordingly, solutions that contain from about 1 to about 20, especially from about 2 to about 15, and very particularly from about 3 to about 8, percent by weight of the desired end product (especially 6-APA, 7-ADCA or 7-ACA) are preferably used.

The time for which the solution to be purified is to be brought into contact with the adsorbent can be greatly varied from a few seconds up to several minutes or even hours. The time depends on the nature and the amount of the adsorbent, the nature and the concentration of the impurities to be removed and the nature of the method and apparatus used. The most advantageous time for a particular case can easily be determined by anyone skilled in the art.

The desired end products can be isolated directly from the crude solutions treated with the adsorbents without further intermediate stages, in the customary manner, for example by acidifying and crystallizing out.

The 6-APA formed by the enzymatic splitting, for example, is isolated, after treatment of the reaction solution according to the invention, according to known processes (see, for example, German Patent Specification No. 1,111,778) and precipitated at pH 4.3.

In order to isolate 7-ADCA and 7-ACA, the solution obtained after treatment with the adsorbent is acidified to pH 3.7 with mineral acid. The 7-ADCA which crystallizes out is filtered off and, for example, washed thoroughly with water and acetone.

Usually it is not necessary further to purify the end products thus obtained before they are used in the production of semi-synthetic β-lactam antibiotics. According to the process of the invention, the end products are not only obtained in outstanding purity but additionally exhibit a relatively coarse crystal grain which makes further industrial processing of the products, for example separating off, washing and drying, simpler as compared with known methods.

The adsorbents used according to the invention can be regenerated after use. They can be used several times over a long period and consequently are particularly economical to use. The regeneration is carried out in the customary manner, according to the instructions of the manufacturer of the particular adsorbent.

Decoloration of the crude solution from the enzymatic cleavage after the treatment with the adsorbents can most appropriately be effected via extinction measurements (for example at 425 nm and a layer thickness of 1 cm). In order to determine the purity of the end products isolated, it is most appropriate to prepare a 10% solution in 2 N hydrochloric acid and to determine their extinctions, for example at 425 nm and a layer thickness of 1 cm.

Crude solutions which can be purified according to the invention are obtainable, for example, as follows.

The cleavage of penicillins with carrier-bonded penicillinacylase (compare, for example, German Offenlegungsschrift No. 2,215,687) can be carried out simply and even on an industrial scale. The carrier-bonded insoluble enzyme is suspended in a solution with 75,000 to 150,000 IU/ml of penicillin, for example penicillin G or penicillin V. The enzymatic cleavage is carried out at a constant pH value in the region of the optimum pH for the bonded penicillinacylase. Aqueous alkali solutions or amines, preferably triethylamine, sodium hydroxide solution or ammonia, are used in order to neutralize the acyl radical which is split off, for example the acyl radical of phenylacetic acid or phenoxyacetic acid. The rate of reaction and the end of cleavage can be seen from the consumption of the base. The reaction temperature is 30° to 45° C., preferably 36° to 38° C. The carrier-bonded enzyme is filtered off and the filtrate is treated with the polymeric adsorbent according to the invention.

7-ADCA, for example, is obtained by enzymatic hydrolysis of 7-phenoxyacetamido-deacetoxycephalosporanic acid or 7-phenylacetamido-deacetoxycephalosporanic acid (compare German Offenlegungsschrift No. 2,355,078). If 7-phenylacetamidodeacetoxycephalosporanic acid (7-BDCA) is used as the starting material, penicillinacylase, preferably carrier-bonded penicillinacylase, can be employed in order to cleave the phenacetyl group enzymatically. 7-BDCA must be previously dissolved in an aqueous suspension by adding alkali, preferably sodium hydroxide solution or ammonia. After adding penicillinacylase, the reaction batch is kept at a pH value of between 7.5 and 8.5 by adding a base, while stirring. Bases which can be used for this purpose are virtually all organic and inorganic bases. Triethylamine, ammonia, sodium hydroxide solution and potassium hydroxide solution are particularly preferred. The rate of reaction and the end of the reaction can be seen easily from the consumption of the base. When the cleavage reaction has ended, the carrier-bonded penicillinacylase is separated off and, according to the invention, the reaction solution is brought into contact with the adsorbent.

The process according to the invention can be demonstrated by the Examples which follow:

A1. Preparation of the carrier 70g of tetraethylene glycol dimethacrylate, 20g of methacrylic acid, 10g of maleic anhydride and 1g of azoisobutyronitrile were dissolved in 1 l of benzene and the batch was first polymerized for 4 hours at 60° C. 1g of azoisobutyronitrile and 200 ml of benzene (boiling point 100°–140° C.) were then added and the batch was polymerized for 2 hours at 70° C. and for 2 hours at 80° C.

The pulverulent polymer was washed thoroughly with petroleum ether (boiling point 30°–50° C.) and dried in vacuo.

| | |
|---|---|
| Yield: | 96 g |
| Bulk volume: | 8.8 ml/g |
| Volume when swollen in water: | 12.4 ml/g |
| Specific surface area: | 8.6 m$^2$/g |
| Acid content after saponification of the anhydride groups | = 3.85 m equivalents/g. |

A2. Preparation of the enzyme resin 15g of the carrier resin prepared according to A1) were suspended in a solution of 1,500 units of penicillinacylase (compare German Offenlegungsschrift No. 2,217,745) in 400 ml of water. The pH value was kept at 6.3 by adding 1 N NaOH, using a pH-stat, and the suspension was stirred for 20 hours at 25° C. It was then filtered through a G-3 glass frit and the material on the frit was washed with 750 ml of a 0.05 M phosphate buffer which had a pH of 7.5 and contained 1 M sodium chloride and with 750 ml of the same buffer without sodium chloride. No further active eluate could be eluted by further washing. The supernatant liquor and the washing solutions were combined and their enzymatic activity was determined. The enzymatic activity of the moist resin was determined for an aliquot amount.

Result

Enzymatic activities (NIPAB test)
Starting solution — 1,500 Units
Supernatant liquor + washing solutions — 280 Units
Carrier resin after the reaction — 1,260 Units The enzymatic activity of the penicillinacylase was determined colorimetrically or titrimetrically using 0.002 M 6-nitro-3-(N-phenylacetyl)-aminobenzoic acid (NIPAB) as the substrate at pH 7.5 and at 25° C. The molar extinction coefficient of the resulting 6-nitro-3-aminobenzoic acid was $E_{405\ nm} = 9090$. 1 unit corresponds to the conversion of 1 mol of substrate per minute.

EXAMPLES 1 TO 8

In each case, 65.5g of potassium penicillin G were dissolved in 1 l of water and hydrolyzed, while stirring, with carrier-bonded penicillinacylase, which contained 1,200 units of penicillinacylase and was prepared according to Example A, to give 6-aminopenicillanic acid (6-APA) and phenylacetic acid. In these cases triethylamine was used to neutralize the phenylacetic acid which was liberated. During the cleavage reaction, the pH value was kept at 7.8 ± 0.2. The temperature of the batch was 37° C. After about 3 hours, the carrier-bonded penicillinacylase was filtered off and 300 ml samples of the solution obtained as the filtrate were filtered through a column (diameter 1 cm) containing 15 ml of an ion exchanger, details of which are set out in the Table I below. The rate of flow was 2 liters per hour. All the ion exchangers used in this Example were in the chloride form.

The extinction of the solution at 425 nm and a layer thickness of 1 cm was measured with a photometer before and after the solution had been filtered through the ion exchanger columns. The values for various types of ion exchangers are also given in Table I.

Table I

| Example No. | Adsorbent | Extinction (425 nm) |
|---|---|---|
| 1 | "Amberlite" IRA 401 | 0.125 |
| 2 | "Amberlite" IRA 900 | 0.111 |
| 3 | "Amberlite" IRA 911 | 0.188 |
| 4 | "Amberlite" IRA 458 | 0.100 |
| 5 | "Amberlyst" A 29 | 0.172 |
| 6 | "Dowex" MSA 1 | 0.112 |
| 7 | "Dowex" 21 K | 0.168 |
| 8 | "Lewatit" MP 500 A | 0.056 |
| Control - no adsorbent | | 0.250 |

EXAMPLE 9

65.5g of potassium penicillin G were hydrolyzed enzymatically according to the procedure of Examples 1 to 8. After separating off the enzyme preparation, the reaction solution was filtered through a column (diameter 2 cm) containing 30 ml of the strongly basic ion exchanger "Lewatit" MP 500 A. The solution was concentrated to 200 ml in vacuo (25 mm Hg) and the pH was adjusted to 4.2 by adding 15% strength (by weight) hydrochloric acid in the presence of 150 ml of methyl isobutyl ketone. The 6-APA which had precipitated was filtered off, washed with water and acetone and dried in vacuo at 40° C.

In order to determine the color content, 2g of the resulting 6-APA were dissolved in 20 ml of 2 N hydrochloric acid and the solution was filtered through a glass fiber filter. The extinctions, measured at 425 nm in a 1 cm cuvette, for 6-APA from three laboratory batches carried out in the same way are listed in Table II below.

Table II

| Yield % of theory | Extinction of a 10% strength solution of 6-APA in 2 N HCl |
|---|---|
| 90.5% | 0.034 |
| 90.2% | 0.056 |
| 92.5% | 0.050 |

Control experiment

When a reaction solution was worked up without the treatment with "Lewatit" MP 500 A, 90.3% of theory of a brownish colored 6-APA were obtained. The extinction measured in hydrochloric acid was 0.31. Because of the high color content, this preparation could not be further processed to give therapeutically utilizable substances without further working up, which, however, would have been associated with a considerable loss in yield. 6-APA which, under the indicated conditions, has extinctions of more than 0.1 and is already slightly yellowish-colored should be excluded from further processing.

EXAMPLE 10

90g of 7-phenylacetamido-deacetoxycephalosporanic acid were suspended in 1.5 l of water and brought into solution at pH 8.0 by adding 20% strength ammonia, while stirring thoroughly. 2,000 units of water-insoluble penicillinacylase, which was prepared according to Example A, were added to the solution. The phenylacetic acid which was liberated during cleavage was neutralized at pH 7.8 ± 0.2 by adding 20% strength ammonia. The temperature of the batch was 37° C. When no further ammonia was taken up, the splitting reaction had ended. The water-insoluble enzyme preparation was separated off and the reaction solution was filtered through a column (diameter 3 cm) containing 100 ml of "Lewatit" MP 500 A in the chloride form. The pH of the eluate was adjusted to 3.7 by adding 12% strength (by weight) sulphuric acid. After leaving the mixture to stand for 3 hours at 5° C., the 7-ADCA which had precipitated was filtered off and washed with 200 ml of water and 200 ml of acetone. It was dried in vacuo at 40° C. The yield was 94% of theory. The extinction of this preparation, determined according to Example 9, was E 0.171.

Control experiment

In an experiment which was carried out in a similar manner but without the treatment with "Lewatit" MP 500 A the 7-ADCA precipitated at pH 3.7 could be separated off by filtration only with difficulty. The yield was 93.5% of theory and the extinction, determined in hydrochloric acid solution according to Example 9 was E 1.02. The preparation was brownish-colored.

The control experiment shows that, without treatment with "Lewatit" MP 500 A a product is formed which cannot directly be utilized therapeutically and the technical isolation of which additionally also presents difficulties.

EXAMPLES 11 TO 14

In each experiment, 7-phenylacetamido-deacetoxycephalosporanic acid was hydrolyzed enzymatically, in 6% strength solution, according to Example 10. After separating off the enzyme resin, 300 ml samples of the solution were filtered, at a throughput of 1.5 l/hour, through columns (diameter 1 cm) containing, in each case, 15 ml of the ion exchanger indicated in Table III below. The extinctions of the reaction solutions after using various ion exchangers are given in Table III.

Table III

| Example No. | Adsorbent | Extinction (425 nm) |
|---|---|---|
| 11 | "Amberlite" IRA 900 | 0.878 |
| 12 | "Amberlite" IRA 458 | 0.73 |
| 13 | "Dowex" MSA 1 | 0.76 |
| 14 | "Lewatit" MP 500 A | 0.642 |

The extinction of the solution before filtration through the column could not be determined without prior dilution. After dilution with water to three times the volume, an extinction of 0.882 was found.

EXAMPLE 15

90g of 7-phenylacetamido-deacetoxycephalosporanic acid were hydrolyzed enzymatically according to Example 10. After separating off the enzyme resin, 100 ml of "Lewatit" MP 500 A in the chloride form were added to the reaction solution. The batch was stirred with the ion exchanger for 2 hours, filtered and further processed as described in Example 10. Yield: 93.8% of theory of 7-ADCA. Extinction, determined in 2 N HCl according to Example 2, E 0.153.

EXAMPLE 16

90g of 7-phenylacetamido-deacetoxycephalosporanic acid are hydrolyzed enzymatically according to Example 10. After separating off the enzyme resin, the reaction solution was filtered through a column (diameter 3 cm) containing "Lewatit" MP 500 A in the nitrate form. The batch was further processed as described in Example 10.

Yield of 7-ADCA — 93.0% of theory
Extinction (425 nm) — 0.174

The procedure of Example 16 was repeated using "Lewatit" MP 500 A in the acetate form in place of "Lewatit" MP 500 A in the nitrate form.

Yield of 7-ADCA — 92.5% of theory
Extinction (425 nm) — 0.188

Control experiment without adsorbent (compare Example 10):
Yield — 93.5% of theory
Extinction (425 nm) — 1.02

Regeneration of the ion exchanger 500 l of "Lewatit" MP 500 A in a 1,000 l stirred kettle were stirred for 15 minutes with alkaline NaCl solution (200 l of water with 5% by weight of NaCl and 5% by weight of NaOH). The ion exchanger was allowed to stand in this solution for 12 hours. Thereafter the salt solution was decanted and the ion exchanger was washed with water. Thorough stirring in alkaline NaCl solution and rinsing were repeated until the salt solution which runs off is colorless. The exchanger was then washed with 5% strength (by weight) sodium chloride solution and water until it was neutral.

What is claimed is:

1. A process for purifying a liquid reaction mixture obtained from the enzymatic cleavage of amido side chains from β-lactam antibiotics, said reaction mixture including the β-lactam antibiotic freed of said side chain, which comprises contacting the reaction mixture with an anion exchange resin, and separating the purified liquid from the resin carrying the impurities.

2. A process according to claim 1, wherein the reaction mixture is separated from the enzyme prior to contact with the adsorbent.

3. A process according to claim 1, wherein the reaction mixture contains by-products which impart color.

4. A process according to claim 1, wherein the anion exchange resin carries quaternary ammonium groups.

5. A process according to claim 4, wherein the anion exchange resin has a macroporous structure and comprises a polystyrene skeleton crosslinked with divinylbenzene.

6. A process according to claim 1, wherein the reaction mixture contains 6-aminopenicillanic acid derived from enzymatic cleavage of a penicillin.

7. A process according to claim 6, wherein the penicillin subjected to said cleavage is benzylpenicillin or phenoxymethylpenicillin, or a salt thereof.

8. A process according to claim 1, wherein the reaction mixture contains 7-amino-deacetoxycephalosporanic acid or 7-aminocephalosporanic acid derived from enzymatic cleavage of a cephalosporin.

9. A process according to claim 8, wherein the cephalosporin subjected to said cleavage is Cephalosporin C or 7-phenylacetamido-deacetoxycephalosporanic acid, or a salt thereof.

10. A process according to claim 1, wherein any enzyme in said reaction mixture is removed, and the reaction mixture is then contacted with the anion exchange resin in a stirred kettle.

11. A process according to claim 1, wherein any enzyme in said reaction mixture is removed, and the reaction mixture is then contacted with the anion exchange resin in a column.

12. A process according to claim 1, wherein any enzyme in said reaction mixture is removed, and the reaction mixture is contacted with the anion exchange resin at a temperature of from about +1° to about +50° C.

13. A process according to claim 1, wherein the reaction mixture contains from about 1 to about 20 percent by weight of the end product to be purified.

14. A process according to claim 1 wherein the purified end product after contact of the reaction mixture with the anion exchange resin in acidified, thereby to precipitate an acidic component formed by the enzymatic cleavage.

15. A process according to claim 14, wherein the end product is obtained in crystalline form.

* * * * *